United States Patent [19]

Stemmler et al.

[11] 4,358,619

[45] Nov. 9, 1982

[54] PROCESS FOR THE PRODUCTION OF LOW MOLECULAR WEIGHT POLYHYDROXYL COMPOUNDS

[75] Inventors: Ingo Stemmler, Odenthal; Hanns P. Müller; Kuno Wagner, both of Leverkusen, all of Fed. Rep. of Germany

[73] Assignee: Bayer Aktiengesellschaft, Leverkusen, Fed. Rep. of Germany

[21] Appl. No.: 13,849

[22] Filed: Feb. 22, 1979

[30] Foreign Application Priority Data

Feb. 25, 1978 [DE] Fed. Rep. of Germany ....... 2808228

[51] Int. Cl.³ .............................................. C07C 27/00
[52] U.S. Cl. .................... 568/388; 568/463; 568/863; 521/175; 528/77
[58] Field of Search ............... 260/594, 602; 568/388, 568/463

[56] References Cited

U.S. PATENT DOCUMENTS

| | | | |
|---|---|---|---|
| 2,224,910 | 12/1940 | Hanford et al. | 260/594 |
| 2,269,935 | 1/1942 | Hanford et al. | 260/594 |
| 2,760,983 | 8/1956 | Maclean et al. | 260/602 |
| 4,156,636 | 5/1979 | Muller et al. | 260/602 |
| 4,219,508 | 8/1980 | Wagner | 568/387 |
| 4,247,653 | 1/1981 | Wagner | 521/158 |

FOREIGN PATENT DOCUMENTS 1088523 10/1980 Canada .
1088558 10/1980 Canada .

*Primary Examiner*—Joseph E. Evans
*Attorney, Agent, or Firm*—Gene Harsh; Joseph C. Gil; Lyndanne M. Whalen

[57] ABSTRACT

The instant invention relates to an improved process for the production of formose from formaldehyde. The improvement resides in using relatively small quanities of basic lead compounds as catalysts for the condensation reaction of the formaldehyde and, at the same time, for controlling the pH-value. By following this technique, organic or inorganic bases which, hitherto, have normally been used for this purpose are no longer needed.

7 Claims, No Drawings

PROCESS FOR THE PRODUCTION OF LOW MOLECULAR WEIGHT POLYHYDROXYL COMPOUNDS

BACKGROUND OF THE INVENTION

In the context of the invention, "formose" is understood to mean the known mixtures of low molecular weight polyhydroxyl compounds (polyhydric alcohols, hydroxy aldehydes and hydroxy ketones) which are formed in the condensation reaction of formaldehyde hydrate.

The production of mixtures of polyhydric alcohols, hydroxy aldehydes and hydroxy ketones from formaldehyde hydrate is known and is described in numerous literature references. In this connection, reference is made, for example, to Butlerow and Loew, Annalen 120, 295 (1861) and J. pr. Chem. 33, 321 (1886); Pfeil Chemische Berichte 84, 229 (1951); Pfeil and Schroth, Chemische Berichte 85, 303 (1952); R. D. Partridge and A. H. Weiss, Carbohydrate Research 24, 29–44 (1972); Emil Fischer's Formoses of Glyceric Aldehyde and Dioxy Acetone; German Pat. Nos. 822,385, 830,951 and 884,794; U.S. Pat. Nos. 2,224,910, 2,269,935 and 2,272,378 and British Pat. No. 513,708.

However, despite the presence of all the prior art noted above no commercially workable process has yet been developed for synthesizing polyhydroxyl compounds by the autocondensation of formaldehyde. This is because the known processes are attended by certain disadvantages such as poor volume-time yields; formation of colored secondary products; inadequate reproductibility of the hydroxyl functionality of the formoses; and the elaborate operations required for removing the bases used as auxiliary reagents. As a result, the synthesis of polyhydroxyl compounds by the autocondensation of formaldehyde hydrate has appeared to be uneconomical and has prevented the autocondensation of formaldehyde hydrate from being used as a basis for a commercial process, for example, for the synthesis of polyhydric alcohols. Due to the simultaneous disproportionation of the formaldehyde into methanol and formic acid, the yields obtained with conventional processes have generally only been moderate, with the result that working up of the aqueous or aqueous/alcoholic formose solutions formed has involved considerable costs.

It is known that the disproportionation of formaldehyde into methanol and formic acid is catalyzed to a large extent by basic compounds. As Pfeil, in Chemische Berichte 84, 229 (1951) observed, the reaction velocity of this so-called "Cannizzaro reaction" is dependent upon the square of the formaldehyde concentration, whereas in the polyaddition of formaldehyde (C-C-linkage) the reaction velocity is linearly dependent upon the formaldehyde concentration (Pfeil and Schroth, Chemische Berichte 85, 303 (1952)). With increasing aldehyde concentration, therefore, the quantitative ratio of the desired polyhydroxyl compounds to methanol and formic acid is displaced against the required compounds. Accordingly, in numerous conventional aldehydes and hydroxy ketones is carried out in solutions having low formaldehyde concentrations in order to keep the quantity of secondary products as small as possible. In order to recover the hydroxy aldehydes and hydroxy ketones formed, however, the water used as solvent has to be removed again by distillation. This involves considerable energy costs because of the intense heat of evaporation of the water. For this reason, processes for the condensation of formaldehyde in dilute aqueous solutions are uneconomical. In addition, decomposition and discoloration reactions involving the hydroxy aldehydes and hydroxy ketones formed generally occur with prolonged distillation times. Accordingly, it is desirable to be able to carry out the condensation of formaldehyde in formalin solutions of standard commercial concentration in the absence of troublesome secondary reactions.

In order to avoid the Cannizzaro reaction, it has also been proposed to carry out the condensation of formaldehyde in solutions in the presence of methanol, ethanol or other polar organic solvents. The addition of organic solvents, however, again reduces the formaldehyde content of the solution. Accordingly, the additional energy costs involved in evaporating the solvent added during the working up of the hydroxy aldehydes and ketones formed also make these processes appear uneconomical. In addition, unstable semiacetals are formed from formaldehyde and lower alcohols. These semiacetals decompose during the condensation reaction with spontaneous liberation of the alcohols. For this reason, considerable delays in boiling occur during condensation reactions carried out at temperatures above the boiling point of the particular alcohol used, particularly in the case of relatively large batches. As a result, the condensation processes cannot be carried out safely on a large scale.

Accordingly, the object of the present invention is to provide a technically simple process by which it is possible to synthesize mixtures of polyhydroxyl compounds substantially free of secondary and decomposition products in favorable volume-time yields. The auxiliary reagents used (catalysts, bases) should easily separable from the reaction products. The mixtures of polyhydroxyl compounds obtained should be colorless and should require no further purification.

Another object of the present invention is to control the autocondensation of formaldehyde in such a way that the product distribution of the mixtures of low molecular weight polyhydroxyl compounds formed may be varied as required and may be reproducibly adjusted.

The solutions to these problems, however, presented difficulties for the following reasons. The normal lead-catalyzed synthesis of formose only takes place if the pH-value of the reaction mixture is adjusted to certain values with additional bases (cf. British Pat. No. 513,708). The alkali hydroxides preferably used for this purpose, however, can only be removed from the reaction product with considerable expense, for example, by using ion exchangers. In general, the tertiary amines often used, even when they are readily volatile as in the case of trimethylamine, can only be quantitatively separated from the formose with ion exchangers (the salts of the amines formed during the reaction cannot be removed from the formose by distillation). The use of ion exchangers for completely desalting the formose is, however, uneconomical, due to the large quantities of waste water involved. One possible answer to these difficulties would be to use basically reacting metal compounds as catalysts, because in this way the quantity of the foreign ions introduced into the formose would remain small.

The calcium hydroxide described by O. LOEW (J. prakt. Chem. 33, 321 (1886) as catalyst base for the production of formose from 4% aqueous formaldehyde would be eminently suitable both for ecological and for economic reasons. Ca(OH)$_2$ catalyzes the formose reaction, simultaneously regulates the pH value of the reaction mixture, and can readily be separated from the reaction product as a non-toxic compound, for example by a precipitation reaction with sulphuric acid. According to E. PFEIL (Chem. Berichte 84, 229 (1951) however, Ca(OH)$_2$ is an extremely effective catalyst for the Cannizzaro reaction. Thus, it is necessary either to accept secondary reactions, which result in reduced yields in the formation of formose, or to use highly dilute formaldehyde solutions, which is also unfavorable for economic reasons.

According to E. PFEIL and to German Pat. No. 822,385, thallium hydroxide is said to give considerably better results than Ca(OH)$_2$ in the synthesis of formose because it selectively catalyzes formose formation at the expense of the Cannizzaro reaction. However, the yields of this process are also relatively low, i.e. from 70 to 80%. Additionally, the extremely high toxicity of the thallium compounds is a deterrent to their commercial use.

The third catalyst base which is known for the synthesis of formose is Pb(OH)$_2$ or PbO. According to German Pat. No. 564,678, a mixture of C$_2$-, C$_3$- and C$_4$-carbohydrates is synthesized from a 4% aqueous formaldehyde solution with the addition of 125 g of Pb(OH)$_2$ per kg of HCHO and is subsequently hydrogenated to form the polyalcohols (65% yield). In addition to a high consumption of energy, however, the working up of reaction mixtures as dilute as these also involves considerable technical outlay.

It is necessary according to U.S. Pat. No. 2,224,910, to add not only from 100 to 150 g of PbO per kg of HCHO, but also to add from 1 to 3% by weight (based on HCHO), of compounds capable of enediol formation as co-catalyst at the beginning of the reaction in the synthesis of formose from 10 to 25% aqueous formaldehyde solutions (74–84% yield). According to this literature reference, the most effective quantity of co-catalyst is from 1 to 10% by weight (based on anhydrous formaldehyde) and any increase in the proportion of enediol formers beyond 10% does not afford any further advantage.

Accordingly, it must be regarded as all the more surprising that, as has now been found, the use of more than 15% by weight (preferably more than 20% by weight and, most preferably more than 40% by weight) of co-catalyst (enediol former) is of particular advantage for converting concentrated aqueous formaldehyde solutions (more than 25% by weight and preferably from 30 to 70% by weight of HCHO) into formose.

In this case, preferably only from about 20 to 80 g and, most preferably, from 30 to 60 g of PbO are required per kg of HCHO. It has also surprisingly been found that corresponding molar quantities of other lead (II) compounds, which have considerably weaker basic properties than PbO, also have good catalytic and adequately basic properties under the conditions of the process. It is particularly surprising, however, that in the process according to the present invention (by comparison with the prior art), it is only necessary to use extremely small base equivalents in the form of basic lead (II) compounds.

DESCRIPTION OF THE INVENTION

Accordingly, the present invention relates to a process for the production of low molecular weight polyhydroxyl compounds comprising autocondensing formaldehyde hydrate in the presence of in water soluble or substantially insoluble compounds of divalent lead as catalyst, said divalent lead being characterized as forming saturated aqueous solution or suspension having a pH value above 4.5, preferably above 5.5 and, most preferably, above 6.0, when mixed with desalted CO$_2$-free water process which is further characterized in that the condensation reaction is carried out in the presence of (a) a quantity of catalyst which corresponds to from 0.1 to 1, preferably from 0.2 to 0.8 and, most preferably, from 0.3 to 0.6 gram equivalents of lead per kg of formaldehyde, (b) more than 15% by weight, preferably more than 20% by weight and, most preferably, more than 40% by weight (based on formaldehyde) of compounds capable of enediol formation as co-catalyst, and optionally (c) low molecular weight and/or relatively high molecular weight polyhydroxyl compounds,
in the absence of further organic or inorganic bases.

By virtue of the substantial suppression of the Cannizzaro reaction, it is possible in accordance with the present invention to obtain (with high reproducibility of the average OH-functionality) from 95 to 98% yields of highly concentrated aqueous solutions of polyols, hydroxy aldehydes and hydroxy ketones. These solutions are completely colorless and therefore require no further purification or decoloration, whereas (as mentioned above), strongly colored, troublesome secondary products which are impossible or extremely difficult and expensive to remove are frequently formed by decomposition reactions when conventional processes are used.

According to the present invention, the autocondensation of formaldehyde hydrate to form hydroxy aldehydes and hydroxy ketones is catalyzed by substantially insoluble and by water-soluble compounds (particularly salts) of divalent lead. In this connection, the lead (II) compounds should be capable of forming saturated solutions or suspensions with fully desalted, CO$_2$-free water having a pH value of $\leq 4.5$ and preferably $\leq 5.5$ and most preferably $\leq 6$. According to the present invention, approximately from 1 to 10% by weight and preferably from 2 to 8% by weight, based on the formaldehyde used, of lead (II) ions are generally used.

According to the present invention, particularly preferred "catalyst bases" are lead oxide (preferably the yellow variant), lead hydroxide, white lead (basic lead carbonate), lead carbonate, lead acetate, basic lead acetate, any basic lead salts (for example PbX(OH), where X is a monovalent anion) and also mixtures of two or more of the above-mentioned catalyst bases. In addition, however, it is also possible to use other basic lead (II) compounds, for example, lead phenolates and lead thiophenolates.

Instead of the readily available and inexpensive PbO, it is also possible to use the substantially insoluble compounds Pb(OH)$_2$ and PbCO$_3$ or basic lead carbonates (for example white lead, Pb(OH)$_2$.2PbCO$_3$) as catalysts under the same or only slightly modified experimental conditions. These substantially insoluble lead bases may be directly added to the reaction mixture in the form of powders, stirrable suspensions (for example in water, formalin, formose or hydrogenated formose, alcohols and also mixtures of these compounds) or pastes (suspended in the above-mentioned liquids). In contrast, readily soluble lead (II) catalyst bases are added to the reaction medium either in the form of powders or, preferably, in the form of solutions (in water, formalin, alcohols or the like). In addition to lead (II) acetate, which may be advantageously used for this purpose, solutions of basic lead (II) salts or solutions of PbO or $Pb(OH)_2$ in lead salt solutions are particularly preferred (lead (II) salt solutions have the advantage of being able to dissolve considerable proportions of the otherwise sparingly soluble lead (II) oxide or hydroxide). Above a certain PbO or $Pb(OH)_2$-content, these solutions show a sufficiently alkaline reaction and, for this reason, represent an excellent, readily measurable formulation for the lead (II) catalyst bases. In this connection, it is particularly preferred to use solutions of PbO or $Pb(OH)_2$ in aqueous lead (II) acetate solutions (so-called "vinegar of lead", Gmelins Handbuch der Anorganischen Chemie, 8th Edition, System No. 47, Verlag Chemie, Weinheim/Bergstr. 1969; pages 772 and 775).

Since they are readily measurable, the solutions of the above-mentioned basic lead (II) salts and solutions of PbO or $Pb(OH)_2$ in lead (II) salt solutions are particularly suitable for controlling pH both in the continuous synthesis and also in the batch synthesis of formose. It is, of course, also possible in accordance with the present invention, however, to control pH during the autocondensation of formaldehyde hydrate with the other substantially insoluble and soluble Pb (II) compounds mentioned above in the described formulations.

Accordiang to the present invention, the autocondensation of formaldehyde hydrate is carried out in the presence of compounds capable of enediol formation as co-catalysts. To this end, the compounds capable of enediol formation are used in quantities of more than 15% by weight, preferably in quantities of more than 20% by weight and, most preferably in quantities of more than 40% by weight, based on formaldehyde. In principle, it is possible for this purpose to use any known compounds which contain a hydroxyl group in the α-position to a carbonyl group, for example, the compounds which are also described as co-catalysts in the above-mentioned literature. According to the present invention, however, preferred co-catalysts are formose itself and oxidation products of polyhydric alcohols containing hydroxyl groups on adjacent carbon atoms (co-catalysts of this particular type are described in detail in German Offenlegungsschrift No. 2,714,084, the disclosure of which is herein incorporated by reference).

In addition to the compounds capable of enediol formation, polyhydroxyl compounds may also be used in the process according to the present invention in a quantity of up to 200% by weight, and preferably in a quantity of from 10 to 100% by weight, based on the formaldehyde used. Compounds of this type are known and are described, for example, in German Offenlegungsschrift No. 2,714,104.

In principle, the quantity of co-catalyst used in accordance with the present invention (based on the formaldehyde present in the reaction mixture) has no upper limit and, as can readily be seen, increases during the condensation reaction (due to the re-formation of formose and to the consumption of formaldehyde). The quantity of co-catalyst may be very considerable, even at the outset, particularly in the continuous process described hereinafter, in which the formaldehyde is added to the reaction mixture either continuously or in portions. For practical reasons, however, the quantity of co-catalyst will generally not exceed 40 times the quantity of formaldehyde present at the beginning of the condensation reaction.

As already mentioned, the conditions under which the process is carried out are generally not critical where the condensation of formaldehyde hydrate is carried out in the presence of basic lead (II) compounds in accordance with the present invention.

The condensation reaction is generally carried out at temperatures above 70° C., preferably at temperatures in the range of from 85° to 150° C. and, most preferably, at temperatures in the range of from 91° to 120° C., the pH value during the reaction is generally in the range of from 3 to 8, preferably in the range of from 3 to 7.5 and, most preferably, in the range of from 3.2 to 7. According to the present invention, aqueous and/or alcoholic formaldehyde solutions and/or paraformaldehyde dispersions containing from 25 to 75% by weight, preferably from 30 to 70% by weight and, with particular preference, from 35 to 65% by weight of formaldehyde are generally used. It is also possible, however, to introduce formaldehyde-containing process gases into co-catalyst-containing absorption liquids and to condense them into formose in these solutions in the presence of the above-mentioned lead (II) catalyst bases according to the invention either in situ or even upon completion of the absorption process. The acid content of these starting components determines the quantity of catalyst base added in accordance with the present invention within the above-mentioned ranges.

According to the present invention, the entire quantity of lead compound may be added at the beginning of the condensation reaction because, by virtue of the substantial suppression of Cannizzaro reactions during formose formation, acids are only formed to a limited extent, so that the pH-value falls only slowly during the condensation reaction.

In some cases (especially in the continuous process described hereinafter), it is best to add the catalyst base either in portions or continuously. It is also possible to influence the reaction velocity as required through the quantity and type of lead compounds added.

The process according to the present invention for the synthesis of formose from formaldehyde hydrate may be carried out either continuously or in batches.

One preferred embodiment of the process starts with methanol-free, standard commercial-grade approximately 37% formalin which contains polyvinyl alcohol for example as stabilizer. The formalin is heated to a temperature of from 95° to 98° C. while being stirred, the necessary amount of co-catalyst according to the invention, namely more than 15% by weight (based on formaldehyde) in formalin or water is added, and the mixture is reheated to from 95° to 98° C. The heat source is removed, after which the entire quantity of yellow lead (II) oxide is introduced into the reaction mixture over a period of from 1 to 5 minutes, so that no residues of PbO adhere to the walls of the reaction vessel. (The residues of PbO outside the liquid phase are completely or partly reduced by formaldehyde vapors into metallic lead which can be washed into the reaction medium. Due to the poor solubility of the Pb-particles, the formose is then clouded and discolored generally by black particles. In addition, formaldehyde condenses from the gas phase on the moist PbO outside the liquid phase to form brown products which discolor the formose and which are difficult to remove). The formose reaction begins immediately and the reaction mixture heats up to boiling point (generally from 99° to 109° C.). The reaction progresses exothermically until it is over. After a total of from about 5 to 30 minutes, the originally milky white, clouded reaction mixture becomes clear because the PbO, most of which was originally present in suspension, gradually passes into solution. After a total of from 10 to 150 minutes, preferably from 15 to 110 minutes and, most preferably, from 20 to 75 minutes, the reaction is terminated at a residual formaldehyde content of from 0 to 8% by weight, preferably from 0.2 to 4% by weight and, most preferably, from 0.4 to 2% by weight, by cooling and/or by the addition of acid, optionally with the simultaneous removal of the catalyst base. In this batch process, the pH value of the reaction mixture is spontaneously adjusted and there is no need for external pH control. (In general, the pH value of the reaction mixture if initially from 4.0 to 7.5, preferably from 4.5 to 6.5, amounting after a 10 to 30% conversion to from 4.0 to 6.5, preferably from 4 to 6, and after a 60 to 95% conversion to from 3 to 5.5 and preferably from 3.5 to 5).

Methanol-containing formaldehyde solutions may, of course, also be used for the production of formose in accordance with the present invention. In this case, the reaction temperatures are correspondingly lower, depending upon the methanol content of the formalin and the resulting reduction in boiling point. Aqueous paraformaldehyde or 1,3,5-trioxane solutions or suspensions may also be used in accordance with the present invention as starting material for the synthesis of formose.

In another preferred variant of the process characterized, in general, by a particularly low consumption of lead (II) compounds, based on the HCHO used, the synthesis of formose is carried out semi-continuously or continuously using relatively large quantities of co-catalyst during the initial phase of the reaction. To begin with, the reaction is started under conditions similar to, or identical with, those used for the batch process and is continued up to the required conversion or residual formaldehyde content. In this case, however, the pH value is preferably kept at a certain value or within a certain pH range (from 3.5 to 6.5 and preferably from 3.8 to 5.8) by adding the catalyst base continuously or in portions. After this batch-type starting phase, formaldehyde is added to the reaction mixture continuously or in portions and, at the same time, the equivalent quantity of reaction product is removed, either continuously or in batches. In addition, the catalyst base is based in such a quantity that the required pH value is maintained. It may be necessary to cool or heat the reaction mixture, depending upon the temperature and quantity of starting components added per unit of time. One particular advantage of the process according to the present invention is that, apart from the reaction temperature, there are only two parameters which have to be watched; namely, the input of formaldehyde and the input of catalyst base. By varying these two parameters, it is possible to determine the pH value and the residence time of the reaction mixture in the reaction zone and, hence, the residual formaldehyde content as well. The product distribution in the formose thus obtained may be readily varied within wide limits and reproduced in this way. During the reaction, the pH is generally maintained at a value of from 3.5 to 6.5, preferably from 3.8 to 5.8 and, most preferably, from 3.8 to 5. The throughput of formaldehyde hydrate amounts to from 0.05 to 5, preferably from 0.1 to 2, and, most preferably, from 0.2 to 1 kg per hour, based on a reactor volume of 1 liter. The temperature in the reaction zone is generally above 70° C., preferably from 85° C. to 150° C. and, most preferably, from 91° to 120° C. After leaving the reaction zone, the product is cooled and/or acid is added in order to terminate the reaction, the lead catalyst optionally being precipitated at the same time. This continuous or semi-continuous variant of the process may be carried out, for example, in cascades of stirrer-equipped vessels which may be operated continuously or even semi-continuously. The production of formose by the process according to the present invention may also be carried out equally favorably in a continuously operated reaction tube into which the catalyst base may be added in the requisite quantity at one or more points of the tube in order to maintain the pH at its required value throughout the entire reaction volume. In this case, too, it is possible to vary the product distribution of the formose within wide limits by varying the throughflow times and the pH-program.

In one particularly preferred and economic embodiment of the process according to the present invention, formose is produced directly, i.e. without any need for formalin or paraformaldehyde, from process gases containing formaldehyde. To this end, the process gases, of the type formed in the production of formaldehyde on a commercial scale, are continuously or periodically passed (preferably without any preceding purification), preferably at temperatures of from 70° to 150° C., into an absorption liquid. This liquid consists of water, optionally monohydric or polyhydric low molecular weight alcohols and/or relatively high molecular weight polyhydroxyl compounds, the compounds capable of enediol formation as co-catalysts and the soluble or insoluble lead (II) compounds as catalyst bases, and has a pH value of from 3 to 8, preferably from 3.5 to 6.5. The formaldehyde is directly condensed in situ in the absorption liquid (optionally even in a following reaction tube or a following cascade of stirrer-equipped vessels), autocondensation of the formaldehyde is terminated at a residual formaldehyde content in the reaction mixture of from 0 to 10% by weight of cooling and/or by deactivating the catalyst with acids and, finally, the catalyst is removed.

Lead-containing catalyst bases are exclusively used in the process according to the present invention. For ecological reasons, however, lead (II) ions should be separated from the crude products before they are offered for sale. This requirement may easily be satisfied without any significant technical or financial outlay.

In one preferred method, the lead (II) ions are electrolytically separated in the form of elemental lead. In this way, it is possible, for example, with suspension electrodes, to obtain residual heavy metal ion contents of 1 ppm or less (cf. the process for removing dissolved heavy metal compounds from effluents described in European Chemical News, Vol. 31, No. 805, page 24 (1977).

The lead separated off may be reused as a catalyst base after conversion into a lead (II) compound. Lead (generally in the form of a melt, having a melting point of 328° C.) is converted into PbO on a commercial scale by treatment with air at an elevated temperature. If the temperature is kept below the melting point of lead oxide (approximately 884° C.), PbO is obtained in the form of a loose, yellow powder (H. Remy, Lehrbuch d.

Anorganischen Chemie, 12th Edition, Leipzig 1965, Vol. I, page 665) which has particularly favorable catalytic properties for the process according to the present invention. The metallic lead may, however, also be recycled by so-called wet conversion. For example, lead dissolves easily in air-containing acetic acid and, after concentration or crystallization at low temperature, may be returned to the formose process as catalytically active lead acetate. Since the mother liquor of the lead acetate may be repeatedly used for dissolving lead, optionally after the addition of more acetic acid, no lead-containing waste products accumulate during the above-described recycling of the lead catalyst.

Another possibility is to separate lead (II) ions electrolytically in the form of $PbO_2$ or simultaneously in the form of Pb and $PbO_2$. Since lead dioxide gives off oxygen, even when gently heated, it can be easily converted back into catalytically active PbO under dry conditions.

Another preferred method of removing the catalyst base from the crude formose is to precipitate the lead (II) ions in the form of a substantially insoluble salt. In principle, it is possible to use salts, for example soda, ammonium carbonate, and sodium hydrogen carbonate as precipitation reagents. Since in this case, however, the cations remain in the formose as new impurities, the addition of salts involves disadvantages. Accordingly, it is preferred to use equivalent quantities or a slight excess of acids for precipitating the lead, the pH value of the crude product advantageously falling at the same time, thereby preventing further condensation of the carbonyl compounds in the product. In principle, it is possible to use any acids which form substantially insoluble salts with lead (II) ions, such as oxalic acid, sulphuric acid, phosphoric acid or hydrogen sulphide.

It is particularly preferred to use oxalic acid because lead oxalate decomposes into a mixture of Pb and PbO at temperatures above 320° C. Lead (II) ions can even be precipitated from formose solutions of high alcohol content (for example methanol or ethanol) at room temperature in the form of lead formate, providing that the water content of the solution is low enough. The lead formate can also be easily decomposed under heat to form Pb and PbO.

In this way, it is possible to completely utilize the lead required for catalysis without fresh quantities of lead being continuously used and harmful waste products being formed. Accordingly, this variant of the process is of particular interest for economic and ecological reasons.

After this purification step, the formose produced in accordance with the present invention advantageously contains only insignificant traces of cationic impurities. Accordingly, there is no need to use cation exchanger resins for removing ions which cannot be separated otherwise (for example alkali or $NH_4^+$). Thus, the frequent regeneration of large quantities of exchanger resins, which always involves large quantities of effluent, is also avoided.

In contrast, any traces of Pb (on the ppm scale) still remaining in the reaction product after precipitation (or electrolysis) may readily be removed with small quantities of cation exchangers. In most cases, however, there is no need for an additional purification step such as this.

Small quantities of organic acids (for example formic acid, lactic acid and saccharic acid) are also formed during the formose reaction. Although they are no problem in many applications, it is advisable in some cases to remove all anions from the formose. Readily volatile acids, for example formic acid, may be distilled off either directly or after acid esterification. In addition, formic acid may also be catalytically decomposed. The residual anions may be removed by means of anion exchangers.

The formoses produced in accordance with the present invention may also be subsequently converted into their semiacetals with excess formaldehyde or may be α-methylolated by reaction with formaldehyde in the presence of bases.

The properties of the formose may be varied within wide limits depending upon the reaction conditions and upon the lines along which condensation reaction of the formaldehyde is carried out. Generally, the average molecular weight and hence the hydroxyl functionality of the formoses is higher, the longer the condensation reaction is continued, i.e. the smaller the amount of residual formaldehyde still present when the condensation reaction is terminated.

In conclusion, it may be stated that the process according to the present invention affords the following significant advantages over conventional processes:

1. The process according to the invention gives mixtures of hydroxy aldehydes, hydroxy ketones and polyhydric alcohols without any troublesome decomposition products.

2. The process according to the invention gives formoses of different OH-functionality whose distribution can be varied as required according to the particular application envisaged. In particular, it is possible to produce mixtures containing more than 90% by weight and, preferably, more than 95% by weight of compounds containing more than 4 carbon atoms. The high reproducibility of the product distribution also represents a significant advantage over conventional processes.

3. The process according to the invention gives colorless products which, after removal of the catalyst base, may be directly hydrogenated without further purification or used for the other purposes mentioned hereinafter.

4. The process according to the invention is particularly economical by comparison with conventional processes. By virtue of the possibility of using highly concentrated formaldehyde solutions or formaldehyde-containing process gases, additional energy costs for evaporating the solvent are avoided. Since virtually no troublesome and undesirable secondary reactions occur in the process according to the invention, yields of from 95 to 98%, based on the formaldehyde used, are obtained. In addition the process according to the invention takes place extremely quickly by comparison with conventional processes and therefore enables extremely high volume-time yields to be obtained.

5. Following their use, the lead-containing catalyst bases employed in the process according to the invention may be reused either directly or after a simple regeneration step so that no ecologically harmful lead-containing waste products are formed.

The formoses obtained in accordance with the present invention and the polyol mixtures ("formitols") obtained from them by hydrogenation (cf. for example German Offenlegungsschriften Nos. 2,714,084 and 2,714,104) are valuable starting materials for a number of commercially interesting products. They are particularly suitable for use as the polyol component in the production of polyurethane plastics.

Accordingly, the present invention also relates to a process for the production of optionally cellular polyurethane plastics by reacting (A) polyisocyanates with (B) low molecular weight polyhydroxyl compounds and, optionally, (C) relatively high molecular weight polyhydroxyl compounds, other chain extenders, blowing agents, catalysts and other known additives, characterized in that the formoses obtained in accordance with the present invention and/or their hydrogenation products are used as component B.

Polisocyanates, relatively high molecular weight polyhydroxyl compounds, chain extenders, blowing agents, catalysts and other additives suitable for the production of polyurethane plastics are known and described, for example, in German Offenlegungsschriften Nos. 2,714,084 and 2,714,104.

The reaction of the polyhydroxyl compounds obtainable in accordance with the present invention (i.e. without any other isocyanate-reactive components) with highly elasticizing polyisocyanates, such as polyisocyanates of biuret structure (German Auslegeschrift No. 1,543,178), lead to hard, light-stable, scratch-resistant and solvent-resistant coatings and lacquers.

By propoxylating and/or ethoxylating the formose and the formitols, it is also possible to obtain polyether alcohols of high functionality which, with high OH-numbers, may be used for the production of rigid and semi-rigid cellular polyurethane plastics and, with low OH-numbers, as starting materials for highly elastic polyurethane foams.

By reacting the formose or the formitol obtained therefrom with polybasic carboxylic acids of the above-mentioned type (for example phthalic acid, isophthalic acid, terephthalic acid, tetra- and hexa-hydrophthalic acid, adipic acid or maleic acid) by known polyester condensation processes, (of the type described, for example, in Houben-Weyl, Methoden der organischen Chemie, Vol. XIV 12, page 40), it is possible to synthesize highly branched polyesters which, when added to alkyd resins, improve their hardness. The polyesters containing hydroxyl groups which are synthesized from the hydroxyl compounds produced in accordance with the present invention may, of course, also be used as starting components for the production of polyurethane plastics.

The formoses and formitols produced in accordance with the present invention may also be reacted very easily with long-chain aliphatic monocarboxylic acids, such as caprylic acid, capric acid, lauric acid, myristic acid, palmitic acid, stearic acid, oleic acid, linoleic acid, arachidonic acid or behenic acid and their derivatives, such as their methyl or ethyl esters or even their anhydrides or mixed anhydrides, to form esters containing hydroxyl groups. These hydroxyl-containing esters represent non-ionic surface-active compounds which may be used as valuable emulsifiers, wetting agents or plasticizers. Thus, these esters are similar to the ethoxylation products of the polyols or even reaction products of the polyhydroxyl compounds obtainable in accordance with the present invention with long-chain monoisocyanates, such as n-octyl, n-decyl, n-dodecyl, myristyl, cetyl or stearyl, isocyanate, i.e. carbamic acid esters (cf. for example, K. Linder, Tenside Vol. III, Wissenschaftliche Verlagsgesellschaft Stuttgart, 1964, page 2336).

The formoses and formitols according to the present invention may also be used as humectants in cosmetics and plastics. They may, however, also be used, for example, as antifreeze agents. They may also be used as carbohydrate-containing substrates in nutrient mediums of microorganisms. Those products which mainly consist of $C_5$ and $C_6$-hydroxy aldehydes and hydroxy ketones have proved to be particularly suitable for this purpose.

The process according to the present invention is illustrated by the following Examples in which the figures quoted represent parts by weight and percent by weight, unless otherwise indicated.

EXAMPLES

EXAMPLE 1

3000 g of a 37% aqueous formaldehyde solution are heated to 93° C. while being stirred, and mixed with 200 g of a 75% aqueous desalted formose solution (produced in accordance with German Pat. No. 884,794). 30 g of PbO are added all at once at an internal temperature of 96° C.

The temperature of the mixture rises to 99° C. and the formose reactions begins. After 10 minutes, another 25 g of PbO are introduced into the reaction mixture. At a residual formaldehyde content of 1.5%, the reaction is terminated after a total of 55 minutes by cooling with ice water. 180 g of a 20% soda solution are added to the reaction mixture at room temperature, followed by stirring for 10 minutes. The lead carbonate is then removed by filtration under suction. After complete desalting over ion exchangers, a formose containing 71.2% of sugar (expressed as glucose) for a water content of 4.8% is obtained in a yield of 92%. Component distribution (in %) after catalytic hydrogenation is as follows:

| $C_2$ | $C_3$ | $C_4$ | $C_5$ | $C_6$ | $C_7$ |
|---|---|---|---|---|---|
| 4.6 | 7.4 | 14.6 | 36.8 | 31.0 | 5.5 |

EXAMPLE 2

(a) Process according to the present invention:

33.5 g of PbO are added, with stirring, at 95° C. to 3000 g of a 37% formalin solution and 246 g of an 86% formose solution in accordance with Example 1, followed by the addition of three further quantities of 5.7 g of PbO at intervals of 8 minutes. After 40 minutes, the solution still contains 4.7% of HCHO. After a total of 55 minutes, the reaction is terminated by cooling at a formaldehyde content of 0%. Initially, a pH value of 6.2 is measured, falling to 5.6 after 3 minutes. The final pH value is 3.65. Working up in the usual way gives a formose having the following characteristics in a yield of 92%: 71.6% sugar (expressed as glucose) and 5.8% of water; viscosity at 20° C./10% water content: 28,600 mPas. Component distribution (in %) after hydrogenation is as follows:

| $C_2$ | $C_3$ | $C_4$ | $C_5$ | $C_6$ | $C_7$ | $C_8$ |
|---|---|---|---|---|---|---|
| 1.4 | 4.0 | 8.8 | 33.8 | 39.7 | 10.9 | 1.5 |

(b) Comparison test (according to U.S. Pat. No. 2,224,910):

If only 24.6 g of the 86% formose solution are used as co-catalyst, together with 3000 g of the 37% formaldehyde solution, it is necessary, in addition to the first 33.5 g of PbO, to add a further nine quantities of 5.6 g of PbO (giving a total of 83.6 g of PbO) at intervals of 7 minutes in order to obtain a residual formaldehyde content of 4.6% in the reaction mixture after 88 minutes.

EXAMPLE 3

27.9 g of PbO (0.125 mol) are introduced at 95° C. into a mixture of 925 g of a 63.3% formalin solution (obtained by concentrating 37% aqueous formaldehyde) and 630 g of the 88.2% formose of Example 5. The pH value of the reaction mixture rises to 5.8 and the internal temperature rises to 104° C. after 5 minutes and to 107° C. after 10 minutes. After a reaction time of 20 minutes, the reaction is terminated by cooling at a residual formaldehyde content of 0.3% and at pH 4.4. Working up in the usual way gives 1156 g of formose containing 66.0% of sugar (expressed as glucose) and 9.5% of water.

A hydrogenated sample of this formose has the following composition (in %):

| $C_2$ | $C_3$ | $C_4$ | $C_5$ | $C_6$ | $C_7$ | $C_8$ |
|---|---|---|---|---|---|---|
| 2.2 | 4.6 | 9.0 | 26.4 | 36.1 | 15.1 | 6.5 |

EXAMPLE 4

1000 g of an 18.5% formalin solution are heated to 95° C. while being stirred, in a reaction vessel. Thereafter 500 g of a 74% formose solution according to Example 1 are added, followed by the introduction of 28.5 g of lead (II) acetate trihydrate (0.075 mol). 1.5 liters of a hot 37% formalin solution are pumped into the reaction mixture over a period of above 20 minutes at 101° C. At the beginning of pumping, 19.0 g of yellow PbO are introduced all at once into the formose/formaldehyde solution. After 20 minutes, the pumping of formalin into the first reaction vessel is interrupted for 5 minutes and, in the meantime, approximately 1.5 liters of reaction mixture are transferred under suction from the first vessel into a flask in which the synthesis of formose is completed over a period of another 20 minutes with stirring and refluxing.

After the formose-formaldehyde mixture has been transferred, the pumping of 1.5 liters of formalin into the first vessel and the operations are repeated another eleven times.

Initially the pH of the solutions is at a value of from 4.3 to 5.0 and, subsequently, from 4.8 to 5.4. During the reaction time of 4.75 hours, a total of 217 g of lead (II) oxide (0.97 mol) is consumed in reacting 20.45 kg of 37% formalin, corresponding to 7.57 kg of anhydrous formaldehyde. (This corresponds to 28.7 g of PbO or 0.257 g-equivalents of PbO per kg of anhydrous HCHO). The residual formaldehyde content in the individual fractions is as follows:

Fraction No./% HCHO: 1/3.6; 2/5.5; 3/3.6; 4/2.3; 5–13/0.6.

One part (A) of the mixture of fractions 5 to 13 is completely desalted over ion exchangers, the other part (B) is freed from lead by electrolysis for 14 hours (110 ppm residual lead). The formoses obtained after concentration of the aqueous solutions contain (A) 69.8% of sugar for a water content of 7.8% and (b) 56.4% of sugar for a water content of 2.1%. According to gas chromatography, the component distribution of the hydrogenated formoses (in %) is as follows:

|   | $C_2$ | $C_3$ | $C_4$ | $C_5$ | $C_6$ | $C_7$ | $C_8$ |
|---|---|---|---|---|---|---|---|
| A | 2.3 | 5.0 | 7.9 | 31.8 | 33.4 | 13.1 | 6.3 |
| B | 1.3 | 3.5 | 5.9 | 31.7 | 36.2 | 15.2 | 6.2 |

EXAMPLE 5

58.2 g of basic lead carbonate (0.225 gram-atoms of Pb) are added over a period of 5 minutes at 97° C. to 3000 g of 37% formalin and 220 g of a 100% formose according to Example 1. The pH value of the reaction mixture rises initially to 4.4 and, in the further course of the reaction, falls to 3.1. After 150 minutes, the reaction is terminated at a 3% residual formaldehyde content by cooling with ice water and by the simultaneous dropwise addition of 29 g of oxalic acid dihydrate in 250 g of water.

After filtration under suction from the deposit, the formose is desalted over anion exchangers and concentrated. A formose containing 11.8% of water and 60.7% of sugar (expressed as glucose) is obtained in a yield of 1233 g.

A hydrogenated sample of this formose has the following component distribution:

|   | $C_2$ | $C_3$ | $C_4$ | $C_5$ | $C_6$ | $C_7$ |
|---|---|---|---|---|---|---|
| % | 6.1 | 7.4 | 12.6 | 30.4 | 36.6 | 6.8 |

EXAMPLE 6

(a) Batch process:

By adding 113.8 g of lead acetate trihydrate (0.3 mol) to 2000 g of 37% formalin and 395 g of 93.7% formose of Example 1 at 96° C., the synthesis for formose is started at pH 5.1. After 25 minutes at 101° C., the formaldehyde content has fallen to 19.5% and the pH value to 4.2. After a total of 70 minutes, the reaction is terminated at a residual formaldehyde content of 1.2% and at a pH value of 3.8. Working up in the usual way gives a formose containing 65.4% of sugar (expressed as glucose) and 6.5% of water. The hydrogenated formose consists of the following components:

| $C_2$ | $C_3$ | $C_4$ | $C_5$ | $C_6$ | $C_7$ | $C_8$ |
|---|---|---|---|---|---|---|
| 3.8 | 5.5 | 9.8 | 25.3 | 40.5 | 12.3 | 3.0 |

(b) Continuous process:

204 g of the 93.7% formose of Example 1 and 100 g of 37% formalin are added to 296 g of boiling water. 60 ml of a 33% solution of lead acetate trihydrate in formalin are run in at 96° C., the pH value of the mixture being spontaneously adjusted to 4.8. After 10 minutes, 650 g of formalin and 120 g of Pb(OOC—CH$_3$)$_2$.(3H$_2$O) are simultaneously added dropwise over a period of 20 minutes. The formaldehyde content of the reaction mixture rises to 14.6%. The introduction of formaldehyde is then interrupted for 30 minutes and is only resumed at 3.5% HCHO and at a pH value of 4.2. By adding more lead acetate, the pH value is maintained at from 4.2 to 4.3, the formaldehyde being introduced in such a quantity that the boiling solution always contains from 2.0 to 5.5% HCHO.

In order to react 7 kg of the 37% formalin over a period of 7 hours, a total of 900 ml of the lead acetate solution is consumed. When the reaction vessel contains around 3500 g of product, fractions of 1000 to 1500 g are removed.

The lead ions are precipitated from the formose solution with oxalic acid. Desalting over anion exchangers and concentration gives 2355 g of a formose containing 64% of sugar (expressed as glucose) and 8.1% of water.

What is claimed is:

1. A process for the production of low molecular weight polyhydroxyl compounds comprising autocondensing formaldehyde hydrate in the presence of soluble or substantially insoluble compounds of divalent lead as catalyst, said divalent lead being capable of forming saturated aqueous solutions or suspensions in desalted, $CO_2$-free water having a pH value of more than 4.5 said process further characterized in that the condensation reaction is carried out in the presence of
   (a) a quantity of catalyst which corresponds to from 0.1 to 1 gram equivalent of lead per kg of formaldehyde,
   (b) more than 15% by weight (based on formaldehyde) of compounds capable of enediol formation as co-catalyst, in the absence of further organic or inorganic bases.

2. A process as claimed in claim 1, characterized in that the catalyst is used in a quantity corresponding to from 0.3 and 0.6 gram equivalent of lead per kg of formaldehyde and the co-catalyst is used in a quantity of more than 40% by weight (based on formaldehyde).

3. A process as claimed in claim 1, characterized in that lead oxide, lead hydroxide, lead carbonate, basic lead carbonate, lead acetate or basic lead acetate is used as the catalyst.

4. A process as claimed in claim 3, characterized in that formose is used as the co-catalyst.

5. A process as claimed in claim 1, characterized in that from 25 to 75% by weight aqueous or alcoholic formaldehyde solutions and/or paraformaldehyde dispersions are used as the formaldehyde source.

6. A process as claimed in claim 1, characterized in that the formaldehyde-containing process gases obtained in the production of formaldehyde on a commercial scale are used as the formaldehyde source.

7. A process as claimed in claim 1, characterized in that the reaction is additionally carried out in the presence of low molecular weight and/or relatively high molecular weight polyhydroxyl compounds.

* * * * *